US007569381B2

(12) United States Patent
Aoyagi

(10) Patent No.: US 7,569,381 B2
(45) Date of Patent: Aug. 4, 2009

(54) BIOCHEMICAL REACTION CASSETTE WITH IMPROVED LIQUID FILLING PERFORMANCE

(75) Inventor: Takaaki Aoyagi, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 541 days.

(21) Appl. No.: 11/515,847

(22) Filed: Sep. 6, 2006

(65) Prior Publication Data

US 2007/0059817 A1 Mar. 15, 2007

(30) Foreign Application Priority Data

Sep. 13, 2005 (JP) ............................ 2005-266023

(51) Int. Cl.
*C12M 1/34* (2006.01)
*C12M 3/00* (2006.01)

(52) U.S. Cl. .................... 435/287.2; 435/6; 435/287.1; 435/293.1

(58) Field of Classification Search ... 435/287.1–288.5, 435/6
See application file for complete search history.

(56) References Cited

U.S. PATENT DOCUMENTS 6,673,620 B1 * 1/2004 Loeffler et al. ................ 436/46
6,677,131 B2 * 1/2004 Yuen ........................... 435/29
6,776,965 B2 8/2004 Wyzgol et al. .............. 422/100
7,204,139 B2 * 4/2007 Takayama ................ 73/204.26
2002/0061529 A1 * 5/2002 Bridgham et al. .............. 435/6
2004/0101870 A1 * 5/2004 Caubet et al. .................. 435/6
2007/0004029 A1 1/2007 Aoyagi .................... 435/287.2
2007/0077645 A1 4/2007 Aoyagi .................... 435/287.2

FOREIGN PATENT DOCUMENTS

JP 2002-243748 8/2002
JP 2003-302399 10/2003
JP 2004-93558 3/2004

* cited by examiner

*Primary Examiner*—Walter D Griffin
*Assistant Examiner*—Shanta G Doe
(74) *Attorney, Agent, or Firm*—Fitzpatrick, Cella, Harper & Scinto

(57) ABSTRACT

A biochemical reaction cassette comprises a housing member, a reaction chamber arranged in the housing member and having a bottom section and a ceiling facing the bottom section, an injection port arranged at the ceiling of the reaction chamber, a discharge port arranged at the ceiling of the reaction chamber and a probe carrier arranged at the bottom section of the reaction chamber, the ceiling having an inclination with the highest part located at the discharge port in the vertical direction.

7 Claims, 6 Drawing Sheets

BIOCHEMICAL REACTION CASSETTE WITH IMPROVED LIQUID FILLING PERFORMANCE

BACKGROUND OF THE INVENTION

1. Field of the Invention

The present invention relates to a biochemical reaction cassette having a probe carrier such as a DNA micro-array that can suitably be used as material for judging the health condition of a subject of examination by examining a specimen for the existence or non-existence of a gene originating from a pathogenic microbe in the specimen, which may typically be a blood specimen. More particularly, the present invention relates to the structure of a biochemical reaction cassette that is not expensive and shows an improved liquid filling performance.

2. Description of the Related Art

Techniques that utilize a hybridization reaction employing a probe carrier, which typically is a DNA micro-array, have been proposed for the purpose of quickly and accurately analyzing the base sequence of a nucleic acid or detecting the target nucleic acid in a nucleic acid specimen. A DNA micro-array is a set of nucleic acid fragments including a fragment having a complementary base sequence relative to that of the target nucleic acid, which fragments are referred to as probe and immobilized highly densely to a solid phase such as beads or a glass plate. The operation of detecting the target nucleic acid using a DNA micro-array generally has the steps as described below.

In the first step, the target nucleic acid is amplified by an amplifying method such as the PCR method. More specifically, the first and second primers are added into the nucleic acid specimen to begin with and a thermal cycle is applied to the specimen. The first primer specifically binds to part of the target nucleic acid while the second primer specifically binds to part of the nucleic acid that is complementary relative to the target nucleic acid. As double-stranded nucleic acids that include the target nucleic acid is combined with the first and second primers, the double-stranded nucleic acids including the target nucleic acid are amplified as a result of an extension reaction. As the double-stranded nucleic acids including the target nucleic acid are amplified sufficiently, the third primer is added to the nucleic acid specimen and a thermal cycle is applied to the specimen. The third primer is labeled with an enzyme, a fluorescent substance, a luminescent substance or the like and specifically combined with part of the nucleic acid that is complementary relative to the target nucleic acid. As the nucleic acid that is complementary relative to the target nucleic acid and the third primer are combined with each other, the target nucleic acid that is labeled with an enzyme, a fluorescent substance, a luminescent substance or the like is amplified as a result of an extension reaction. Then, consequently, the labeled target nucleic acid is produced when the nucleic acid specimen contains the target nucleic acid, whereas no labeled target nucleic acid is produced when the nucleic acid specimen does not contain the target nucleic acid.

In the second step, the nucleic acid specimen is brought into contact with a DNA micro-array to give rise to a hybridization reaction with the probe of the DNA micro-array. More specifically, the temperature of the DNA micro-array and the nucleic acid specimen is raised. Then, at this time, the probe and the target nucleic acid form a hybrid when the target nucleic acid is complementary relative to the probe.

In the third step, the target nucleic acid is detected. If, for instance, the labeling substance is a fluorescent one, the fluorescent substance is energized typically by means of a laser and the luminance of the energized substance is observed. In other words, it is possible to detect if the probe and the target nucleic acid has produced a hybrid or not by means of the labeling substance of the target nucleic acid and hence the presence or absence of a specific base sequence can be confirmed.

DNA micro-arrays adapted to utilize a hybridization reaction are expected to find applications in the field of medical diagnosis for identifying specific pathogenic microbes and gene diagnosis for examining bodily constitutions of patients. However, as a matter of fact, the step of amplification of the nucleic acid, that of hybridization and that of detection of the target nucleic acid as listed above are conducted normally individually by means of respective apparatus and involve cumbersome operations to make the diagnosis considerably time consuming. Particularly, when the hybridization reaction is made to take place on a glass slide, the probe can become missing or contaminated when the operator touches the glass slide with a fingertip because the probe-immobilizing region is exposed. Therefore, the operator is required to handle the probe very carefully. To avoid these and other problems, there have been proposed several biochemical reaction cassettes having a structure adapted to arrange a DNA micro-array in a reaction chamber, make a hybridization reaction to take place in the reaction chamber and conduct the subsequent detection step also in the reaction chamber.

FIGS. 7 and 8 illustrate such a biochemical reaction cassette. FIG. 8 is a cross sectional view of the biochemical reaction cassette of FIG. 7 taken along a plane parallel to the vertical direction that includes the injection port and the discharge port. Referring to FIGS. 7 and 8, the biochemical reaction cassette 51 comprises a housing 52 and a glass substrate 53 to which a DNA probe that is to specifically bind to a target nucleic acid is immobilized. The housing 52 is provided with a dent section (recess) and part of the recess forms a reaction chamber 54 having a bottom surface where the DNA probe is immobilized as the housing 52 and the glass substrate 53 are bonded to each other. An injection flow channel 55 and a discharge flow channel 56 are connected to the reaction chamber 54 so that the liquid specimen to be analyzed and one or more than one reagents may be injected and discharged.

The reaction chamber 54 of the biochemical reaction cassette 51 as illustrated in FIGS. 7 and 8 has only a small volume of tens of several microliters and bubbles are apt to remain in the reaction chamber 54 after filling it with liquid due to its structure. The biochemical reaction can be blocked and the diagnosis can be adversely affected when bubbles remain in the region where the DNA probe is immobilized to the glass substrate 53. The operation of precisely controlling the movement of liquid so that bubble may not remain in the reaction chamber 54 is a cumbersome one and additionally such bubbles can form an obstacle when the biochemical reaction cassette is applied to an automatic diagnostic apparatus. To avoid this problem, Japanese Patent Application Laid-Open No. 2003-302399 discloses an arrangement where the reaction chamber is provided on the upper or lower surface thereof with a hydrophobic region and a hydrophilic region. Japanese Patent Application Laid-Open No. 2004-093558 discloses an arrangement for preventing bubbles from being produced by means of a flow channel formed by using a protruding member in an upper part of the reaction region. Japanese Patent Application Laid-Open No. 2002-243748 discloses an arrangement for forming a uniformly spreading flow of liquid by means of a butterfly structure or a cascade structure.

The arrangement of Japanese Patent Application Laid-Open No. 2003-302399 and that of Japanese Patent Application Laid-Open No. 2004-093558, however, cannot completely eliminate bubbles remaining at and near the outlet port. Similarly, with the arrangement of Japanese Patent Application Laid-Open No. 2002-243748, bubbles may be left in an upper part of the reaction chamber because the outlet port is connected to an end of the chamber. When bubbles are left at and near the outlet port, they can grow in the hybridization step to cover the DNA probe-immobilizing region because of the temperature rise in that step. Then, the biochemical reaction can be blocked to adversely affect the diagnosis.

Additionally, the arrangements of Japanese Patent Application Laid-Open No. 2003-302399, Japanese Patent Application Laid-Open No. 2004-093558 and Japanese Patent Application Laid-Open No. 2002-243748 require the cassette to be surface-treated and involve a complex profile for the reaction chamber to consequently raise the cost of manufacturing the cassettes.

SUMMARY OF THE INVENTION

In view of the above identified problems of the prior art, it is therefore the object of the present invention to provide a biochemical reaction cassette with an improved performance for being filled with liquid so as to allow a biochemical reaction to be reliably conducted at low cost.

According to the present invention, the above object is achieved by providing a biochemical reaction cassette comprising: a housing member; a reaction chamber arranged in the housing member and having a bottom section and a ceiling facing the bottom section; an injection port arranged at the ceiling of the reaction chamber; a discharge port arranged at the ceiling of the reaction chamber; and a probe carrier arranged at the bottom section of the reaction chamber, wherein the ceiling has an inclination with the highest part located at the discharge port in the vertical direction.

According to the present invention, as the ceiling of the reaction chamber is provided with an inclination toward the discharge port, the discharge port is located at the highest part of the inclination. Thus, as the reaction chamber is filled with liquid, gas whose specific gravity is small is collected at the highest part of the ceiling. In other words, as the reaction chamber is filled with liquid, gas is discharged to the outside of the reaction chamber by way of the discharge flow channel and liquid starts flowing into the discharge flow channel only when gas is totally eliminated from the reaction chamber. As a result, it is possible to prevent bubbles from remaining in the reaction chamber.

Additionally, whenever necessary, the injection flow channel and the discharge flow channel may be arranged perpendicularly relative to the reaction surface of the probe carrier to make the biochemical reaction cassette moldable by means of a metal mold. Still additionally, the liquid reservoir chamber may be arranged at the side of the housing member opposite to that of the reaction chamber. With this arrangement, again, it is possible to mold the biochemical reaction cassette by means of a metal mold.

With this arrangement, it is possible to provide a biochemical reaction cassette that is not expensive and shows an improved liquid filling performance.

Other features and advantages of the present invention will become apparent from the following description taken in conjunction with the accompanying drawings, in which like reference characters designate the same or similar parts throughout the figures thereof.

Further features of the present invention will become apparent from the following description of exemplary embodiments with reference to the attached drawings.

DESCRIPTION OF THE EMBODIMENTS

Figure 1:
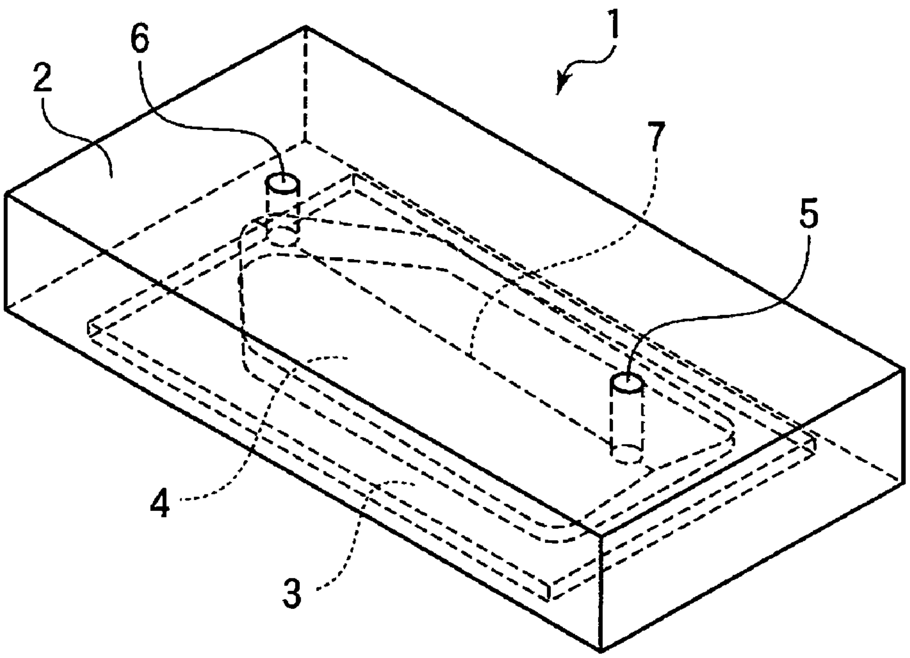
FIG. 1 is a schematic perspective view of the first embodiment of biochemical reaction cassette according to the present invention, illustrating the structure thereof.

Preferred embodiments of the present invention will now be described in detail in accordance with the accompanying drawings.

A biochemical reaction cassette according to the present invention comprises a housing member and a reaction chamber arranged in the housing, on the bottom of which a probe carrier is arranged so that it may be brought into contact and react with a specimen liquid put into it. The operation of injecting liquid into and discharging liquid from the reaction chamber is conducted respectively by way of an injection flow channel and a discharge flow channel connected to the reaction chamber. An injection port and a discharge port are arranged at the ceiling of the reaction chamber to connect the reaction chamber and the injection flow channel and the discharge flow channel respectively. Additionally, the ceiling of the reaction chamber is provided with an inclined section that is inclined toward the discharge port. The inclined section shows a continuous inclination from the lowest part toward the highest part thereof in the vertical direction and is formed such that the discharge port is located at the highest part. The expression of vertical direction as used herein refers to the vertical direction in a state where the biochemical reaction cassette is placed in position on a measuring instrument or the like. Normally, a biochemical reaction cassette according to the present invention is mounted in a measuring instrument (not shown) with the bottom section thereof directed perpendicular relative to the vertical direction. The ceiling of a biochemical reaction cassette according to the present invention refers to the inner wall surface disposed vis-à-vis the bottom section in the reaction chamber. Since the ceiling of the reaction chamber is provided with an inclined section that is inclined toward the discharge port, the distance separating the bottom section and the discharge port is greater than the distance separating the bottom section and the injection port.

A probe carrier to be mounted in a biochemical reaction cassette according to the present invention is formed by immobilizing a probe that can specifically bind to a target nucleic acid to be detected to a carrier, which may typically be a substrate, although the structure thereof may be selected depending on the application of the biochemical reaction cassette. A DNA micro-array may be used for a probe carrier for the purpose of the present invention.

A biochemical reaction cassette according to the present invention may have a structure where a dent section (recess) is formed on a predetermined surface of the housing member and is hermetically sealed by a probe carrier. With such an arrangement, the bottom section of the recess agrees with the ceiling of the reaction chamber so that it is made to show the above-described structure of the ceiling. When the reaction chamber has such a structure, it is possible to mold the housing member by means of a metal mold.

Preferably, the injection flow channel and the discharge flow channel are arranged in parallel with each other and extend linearly in the vertical direction.

A biochemical reaction cassette according to the present invention may further comprise a liquid reservoir chamber for injection located above the reaction chamber and connected to the latter by way of the injection flow channel. Such a liquid reservoir chamber is made to show a cross sectional area greater in the cross section perpendicular to the direction of liquid flow (the direction of the flow channel) than in the cross section in the direction of the injection flow channel. Additionally, biochemical reaction cassette according to the present invention may further comprise a discharged liquid reservoir chamber located above the reaction chamber and connected to the latter by way of the discharge flow channel. Such a liquid reservoir chamber is also made to show a cross sectional area greater in the cross section perpendicular to the direction of liquid flow (the direction of the flow channel) than in the cross section in the direction of the discharge flow channel. Either or both of these liquid reservoir chambers may be arranged in the housing member. The reaction chamber may be made to show a tapered profile where the cross sectional area of the reaction chamber is gradually reduced in the plane perpendicular to the direction of liquid flow from the injection port toward the discharge port.

With any of the above-described additional arrangements, it is possible to further improve the performance of a biochemical reaction cassette according to the present invention in terms of filling the reaction chamber with liquid.

Now, the present invention will be described further by referring to the accompanying drawings that illustrate preferred embodiments of the invention.

First Embodiment

Figure 2:
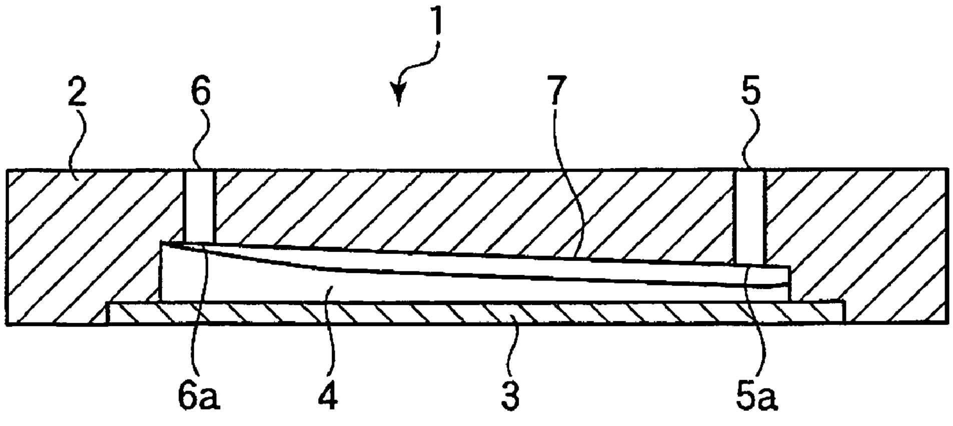
FIG. 2 is a schematic cross sectional view of the biochemical reaction cassette of FIG. 1, illustrating the structure thereof.

FIG. 1 is a schematic perspective view of the first embodiment of biochemical reaction cassette according to the present invention, illustrating the structure thereof. FIG. 2 is a schematic cross sectional view of the biochemical reaction cassette of FIG. 1 taken along a plane parallel to the vertical direction that includes the injection port and the discharge port of the biochemical reaction cassette.

Firstly, the structure of the biochemical reaction cassette of this embodiment will be described below. The biochemical reaction cassette 1 comprises a housing 2 made of polycarbonate and a glass substrate 3, which is bonded to the housing 2 and to which a DNA probe that is to specifically bind to a target nucleic acid is immobilized. Note that the mode of bonding the glass substrate 3 to the housing 2 is not limited to the illustrated one and the glass substrate 3 may be bonded to the housing 2 in any of various alternative modes. The material of the housing 2 is not limited to polycarbonate and the housing 2 may alternatively be made of a plastic material other than polycarbonate, glass, rubber, silicones or some other appropriate material. Similarly, the material of the glass substrate 3 is not limited to glass and plastics, silicones or some other appropriate material may be used for it. A recess having a predetermined cross sectional contour is formed on the surface of the housing 2 bonded to the glass substrate 3 to provide a reaction chamber 4 between the housing 2 and the glass substrate 3. The part of the surface of the glass substrate 3 that operates as the bottom surface of the reaction chamber 4 is provided with a probe-immobilizing region (not shown). Thus, when the nucleic acid specimen solution filled in the reaction chamber 4 contains the target nucleic acid, the target nucleic acid produces a hybrid with the probe in the probe-immobilizing region. The combination of a target nucleic acid and a probe can be selected appropriately (e.g. both of them being DNAs) according to the objective of detection. An injection flow channel 5 and a discharge flow channel 6 are connected to the reaction chamber 4 respectively by way of an injection port 5*a* and a discharge port 6*a* so that liquid may be injected into and discharged from the reaction chamber 4. The line connecting the injection flow channel 5 and the discharge flow channel 6 on the ceiling of the reaction chamber 4 has a vertex section 7, which is higher than any other part in the cross section of the reaction chamber perpendicular to the direction of liquid flow (the direction from the discharge port 6*a* to the injection port 5*a*). Additionally, the ceiling of the reaction chamber 4 is provided with an inclined section that is inclined from the injection port 5*a* toward the discharge port 6*a* so that the vertex section 7 itself may constantly and continuously be located at a high position.

The target nucleic acid can be detected by means of the biochemical reaction cassette 1 and a detection method as will be described below. Firstly, a nucleic acid specimen is prepared and, if necessary, the target nucleic acid is amplified by means of the above-described method. When the nucleic acid specimen contains the target nucleic acid, the target nucleic acid that is labeled by a fluorescent substance is produced in the amplification step. While the labeling substance is a fluorescent substance in the above description, it may alternatively be a luminescent substance or an enzyme. The nucleic acid specimen solution is then injected into the biochemical reaction cassette 1 from the injection flow channel 5 by means of a liquid injection means (not shown).

Now, how the nucleic acid specimen solution is filled into the reaction chamber 4 will be described below. As the nucleic acid specimen solution is injected from the injection flow channel 5, it flows in the reaction chamber 4 from the injection flow channel 5 toward the discharge flow channel 6. The wall of the reaction chamber 4 is provided with a tapered section where the cross sectional area of the reaction chamber 4 is gradually reduced toward the discharge flow channel 6 and the nucleic acid specimen solution injected from the injection flow channel 5 is collected in the discharge flow channel 6 as it flows in the reaction chamber 4. Under a condition where the nucleic acid specimen solution is filled to a certain extent, all the surface of the glass substrate 3 that constitutes part of the wall surface of the reaction chamber 4 is held in contact with the nucleic acid specimen solution and gas is left in the vertex section 7. As the nucleic acid specimen solution is supplied further, the gas in the reaction chamber 4 is driven toward the discharge flow channel 6 and to a higher part in the vertex section 7. Eventually, as a result, after the gas left in the reaction chamber 4 is driven off to the outside from the discharge flow channel 6 and completely eliminated from the reaction chamber 4, the nucleic acid specimen solution flows into the discharge flow channel 6. Thus, the reaction chamber 4 is completely filled with the nucleic acid specimen solution.

When the reaction chamber 4 is filled with the nucleic acid specimen solution, the nucleic acid specimen solution is heated to cause the hybridization reaction between the target nucleic acid in the nucleic acid specimen solution and the probe on the glass substrate 3 to proceed. Since no gas is left in the reaction chamber 4 when the latter is filled with liquid, there is no risk that the hybridization reaction is retarded because the nucleic acid specimen solution and the probe do not contact each other. When the hybridization reaction is completed, the nucleic acid specimen solution is discharged from the discharge flow channel 6. Subsequently, the reaction product of the hybridization reaction on the glass substrate 3 is detected by a detection means (not shown) and the fluorescent label.

As described above, the structure where an inclination is formed to the ceiling of the reaction chamber 4 and directed toward the discharge flow channel 6 is simple and improves the liquid filling performance of the reaction chamber 4. Then, as a result, it is possible to avoid any erroneous judgment on the detection of a hybridization reaction product that may arise due to a situation where the probe on the glass substrate and the nucleic acid specimen solution are not brought into contact with each other and hence no biochemical reaction takes place there. Additionally, since the biochemical reaction cassette 1 has a structure that can be manufactured by means of a metal mold, it is possible to reduce the manufacturing cost of the biochemical reaction cassette 1.

Second Embodiment

Figure 3:
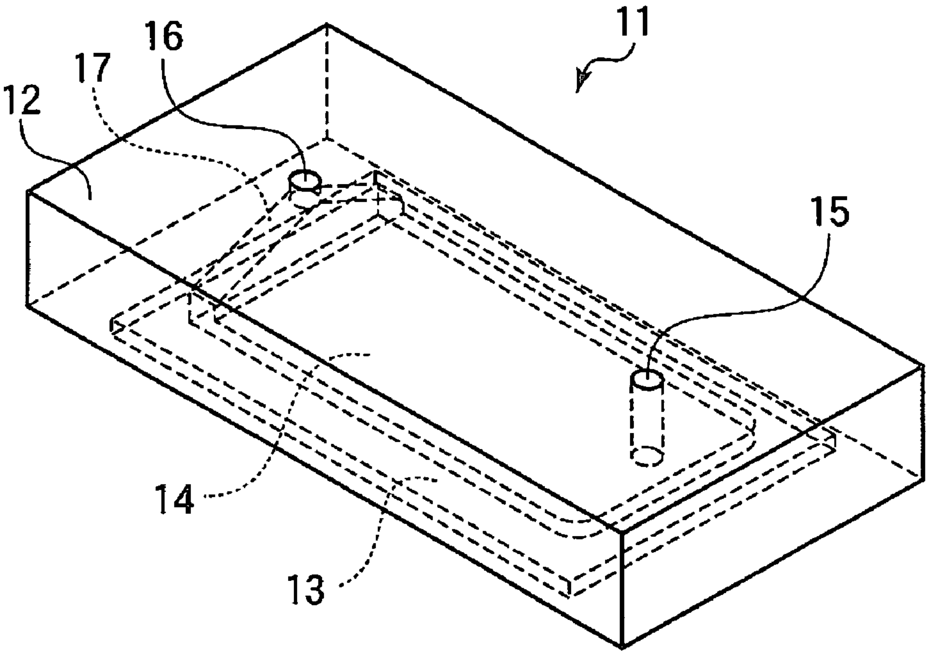
FIG. 3 is a schematic perspective view of the second embodiment of biochemical reaction cassette according to the present invention, illustrating the structure thereof.
Figure 4:
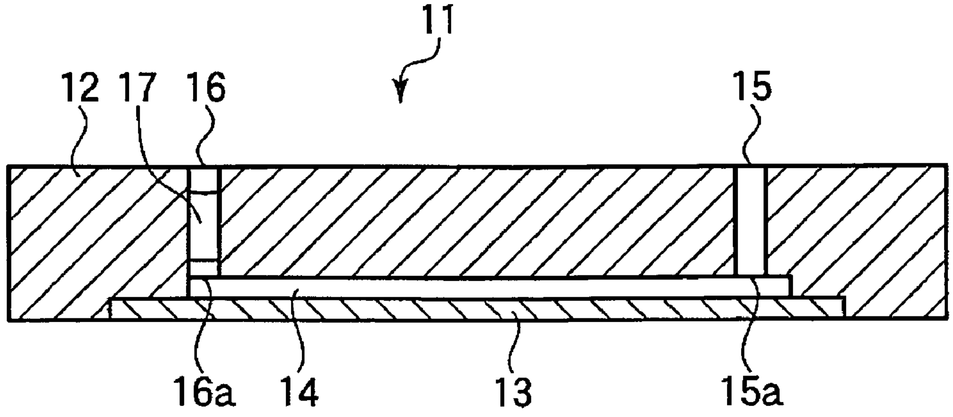
FIG. 4 is a schematic cross sectional view of the biochemical reaction cassette of FIG. 3, illustrating the structure thereof.

FIG. 3 is a schematic perspective view of the second embodiment of biochemical reaction cassette according to the present invention, illustrating the structure thereof. FIG. 4 is a schematic cross sectional view of the biochemical reaction cassette of FIG. 3, taken along a plane parallel to the vertical direction that includes the injection port and the discharge port of the biochemical reaction cassette.

Firstly, the structure of the biochemical reaction cassette of this embodiment will be described below. The biochemical reaction cassette 11 comprises a housing 12 made of polycarbonate and a glass substrate 13, which is bonded to the housing 12 and to which a DNA probe that is to specifically bind to a target nucleic acid is immobilized. Note that the mode of bonding the glass substrate 13 to the housing 12 is not limited to the illustrated one and the glass substrate 13 may be bonded to the housing 12 in any of various alternative modes. The material of the housing 12 is not limited to polycarbonate and the housing 12 may alternatively be made of a plastic material other than polycarbonate, glass, rubber, silicones or some other appropriate material. Similarly, the material of the glass substrate 13 is not limited to glass and plastics, silicones or some other appropriate material may be used for it. A recess having a predetermined cross sectional contour is formed on the surface of the housing 12 bonded to the glass substrate 13 to provide a reaction chamber 14 between the housing 12 and the glass substrate 13. The part of the surface of the glass substrate 13 that operates as the bottom surface of the reaction chamber 14 is provided with a probe-immobilizing region (not shown). Thus, when the nucleic acid specimen solution filled in the reaction chamber 14 contains the target nucleic acid, the target nucleic acid produces a hybrid with the probe in the probe-immobilizing region. The combination of a target nucleic acid and a probe can be selected appropriately (e.g. both of them being DNAs) according to the objective of detection. A buffer section 17 is arranged at an end of the reaction chamber 14 on the ceiling. The buffer section 17 extends in the vertical direction from the ceiling of the reaction chamber 14 and a discharge flow channel 16 is connected to the upper surface of the buffer section 17 by way of a discharge port 16*a*. The buffer section 17 is provided with a tapered profile where the cross sectional area of the buffer section 17 is gradually reduced toward the discharge flow channel. An injection flow channel 15 is connected to the ceiling of the reaction chamber 14 at a position opposite to the position where the ceiling is connected to the buffer section.

The target nucleic acid can be detected by means of the biochemical reaction cassette 11 and a detection method as will be described below. Firstly, a nucleic acid specimen is prepared and, if necessary, the target nucleic acid is amplified by means of the above-described method. When the nucleic acid specimen contains the target nucleic acid, the target nucleic acid that is labeled by a fluorescent substance is produced in the amplification step. While the labeling substance is a fluorescent substance in the above description, it may alternatively be a luminescent substance or an enzyme. The nucleic acid specimen solution is then injected into the biochemical reaction cassette 11 from the injection flow channel 15 by means of a liquid injection means (not shown).

Now, how the nucleic acid specimen solution is filled into the reaction chamber 14 will be described below. As the nucleic acid specimen solution is injected from the injection flow channel 15 by way of the injection port 15*a*, it flows in the reaction chamber 14 from the injection flow channel 15 toward the buffer section 17. Since the buffer section 17 is located at a position higher than the reaction chamber 14, no nucleic acid specimen solution flows into the buffer section 17 until the reaction chamber 14 is completely filled with the nucleic acid specimen solution. As the reaction chamber 14 is filled with the nucleic acid specimen solution, the nucleic acid specimen solution flows into the buffer section 17 to gradually raise the level of the solution in the buffer section 17. Since the ceiling of the buffer section 17 is tapered toward the discharge flow channel 16, the gas left in an upper part of the buffer section 17 is expelled gradually to the outside from the discharge flow channel 16. Since the nucleic acid specimen solution flows into the discharge flow channel 16 only when the gas is completely eliminated from the buffer section 17, the reaction chamber 14 and the buffer section 17 come to be completely filled with the nucleic acid specimen solution.

When the reaction chamber 14 is filled with the nucleic acid specimen solution, the nucleic acid specimen solution is heated to cause the hybridization reaction between the target nucleic acid in the nucleic acid specimen solution and the probe on the glass substrate 13 to proceed. Since no gas is left in the reaction chamber 14 when the latter is filled with liquid, there is no risk that the hybridization reaction is retarded because the nucleic acid specimen solution and the probe do not contact each other. When the hybridization reaction is completed, the nucleic acid specimen solution is discharged from the discharge flow channel 16. Subsequently, the biochemical reaction cassette 11 is set in position in a detection apparatus (not shown) and the reaction product of the hybridization reaction on the glass substrate 13 is detected by means of the fluorescent label.

As described above, the structure where a buffer section 17 is arranged at the ceiling of the reaction chamber 14 and an inclination is formed to the ceiling of the buffer section 17 and directed toward the discharge flow channel 16 is simple and improves the liquid filling performance of the reaction chamber 14. Then, as a result, it is possible to avoid any erroneous judgment on the detection of a hybridization reaction product that may arise due to a situation where the probe on the glass substrate and the nucleic acid specimen solution are not brought into contact with each other and hence no biochemical reaction takes place there. Additionally, since the biochemical reaction cassette 11 has a structure that can be manufactured by means of a metal mold, it is possible to reduce the manufacturing cost of the biochemical reaction cassette 11.

Third Embodiment

Figure 5:
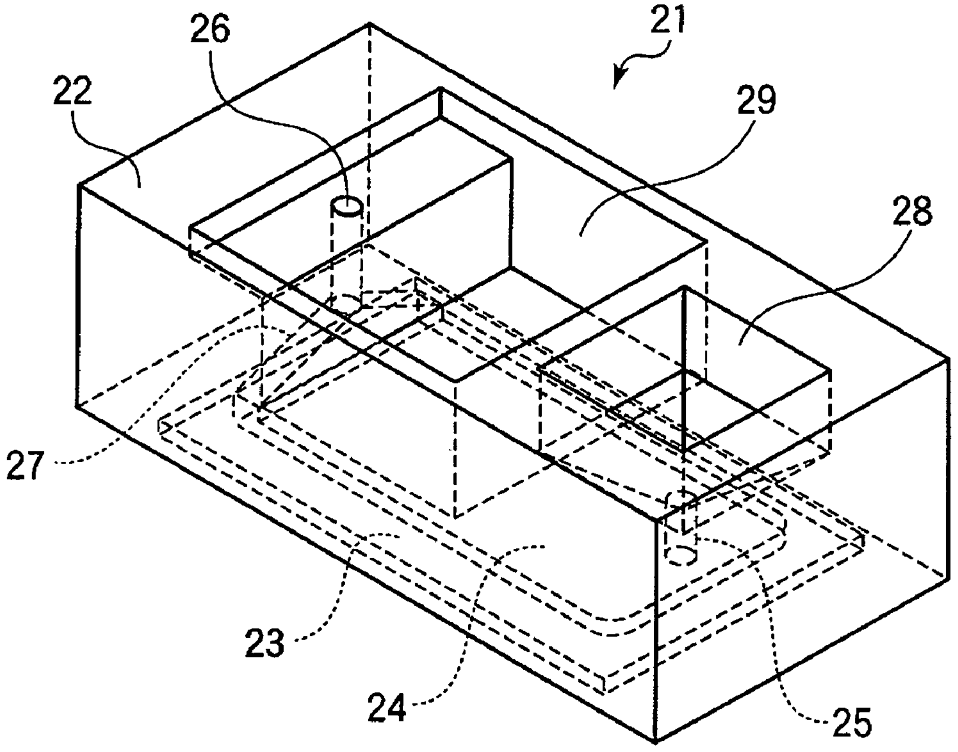
FIG. 5 is a schematic perspective view of the third embodiment of biochemical reaction cassette according to the present invention, illustrating the structure thereof.
Figure 6:
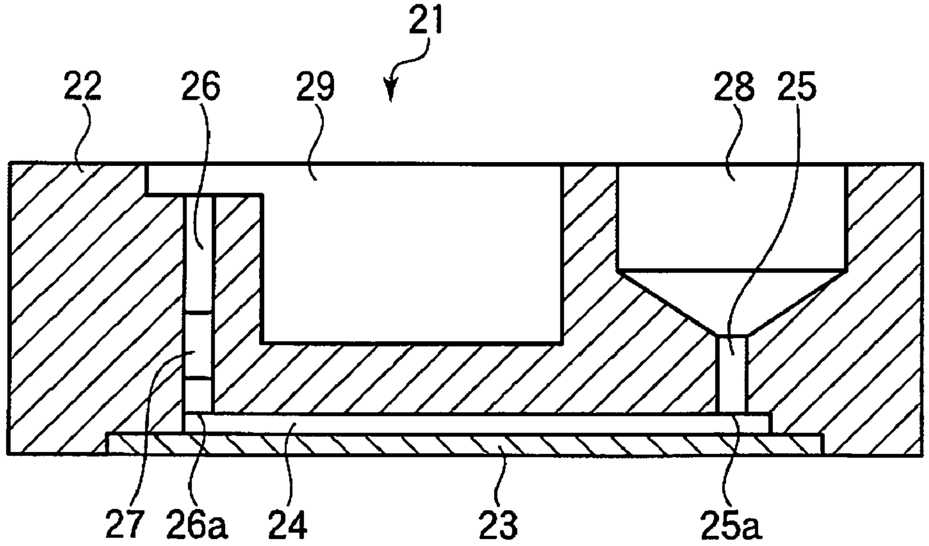
FIG. 6 is a schematic cross sectional view of the biochemical reaction cassette of FIG. 5, illustrating the structure thereof.
Figure 7:
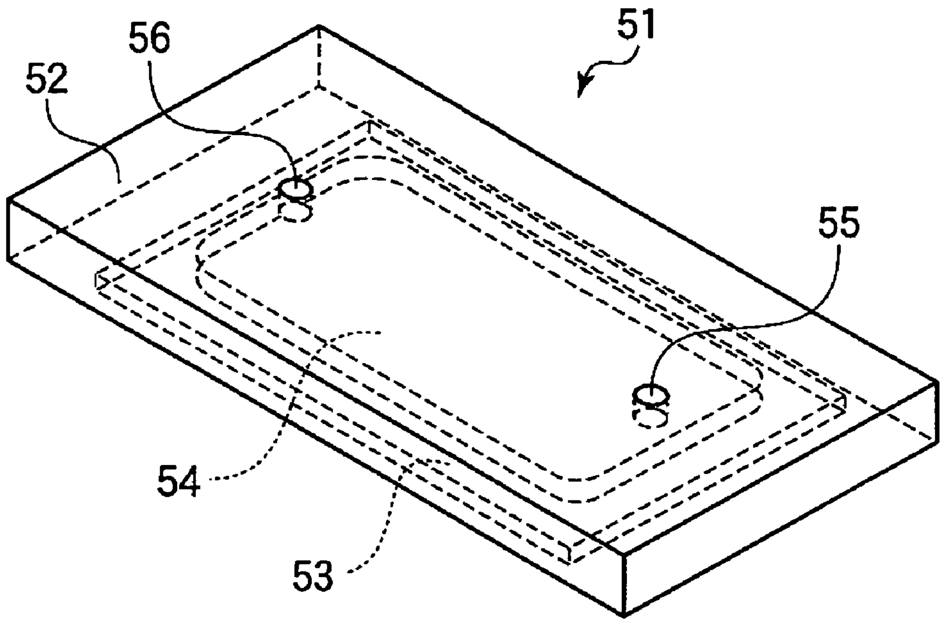
FIG. 7 is a schematic perspective view of a known biochemical reaction cassette, illustrating the structure thereof.
Figure 8:
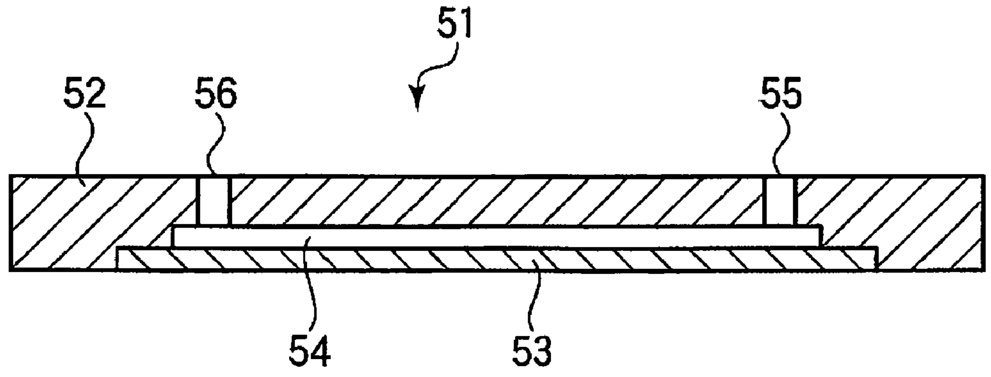
FIG. 8 is a schematic cross sectional view of the known biochemical reaction cassette of FIG. 7, illustrating the structure thereof.

FIG. 5 is a schematic perspective view of the third embodiment of biochemical reaction cassette according to the present invention, illustrating the structure thereof. FIG. 6 is a schematic cross sectional view of the biochemical reaction cassette of FIG. 5, taken along a plane parallel to the vertical direction that includes the injection port and the discharge port of the biochemical reaction cassette.

The biochemical reaction cassette 21 comprises a housing 22 and a glass substrate 23, which is bonded to the housing 22 and to which a DNA probe that is to specifically bind to a target nucleic acid is immobilized. Since this embodiment is provided with a reaction chamber 24, an injection flow channel 25, a discharge flow channel 26 and a buffer section 27, which are like those of the second embodiment, they will not be described here any further. The end of the injection flow channel 25 that is not connected to the reaction chamber 24 is connected to a liquid reservoir chamber 28. The end of the discharge flow channel 26 that is not connected to the buffer section 27 is connected to a waste liquid reservoir chamber 29.

To fill the reaction chamber 24 of the biochemical reaction cassette 21 with a nucleic acid specimen solution, firstly the nucleic acid specimen solution is supplied to the liquid reservoir chamber 28 by a liquid supply means (not shown). At this time, since the cross sectional area of the injection flow channel 25 is smaller than that of the liquid reservoir chamber 28, the nucleic acid specimen solution does not flow into the reaction chamber 24 due to the resistance of the injection flow channel 25 if the nucleic acid specimen solution is simply supplied to the liquid reservoir chamber. Therefore, the nucleic acid specimen solution is introduced into the reaction chamber 24 and the buffer section 27 by bringing the side of the waste liquid reservoir chamber 29 under negative pressure by a negative pressure generation means (not shown) such as a suction pump. On the principle same as the one described above for the second embodiment, no gas is left in the reaction chamber 24 and the reaction chamber 24 can be completely filled with the nucleic acid specimen solution. A hybridization reaction is made to take place under the condition where both the reaction chamber 24 and the buffer section 27 are filled with the nucleic acid specimen solution. When the hybridization reaction comes to an end, the side of the waste liquid reservoir chamber 29 is again brought under negative pressure by a negative pressure generation means (not shown) to cause the nucleic acid specimen solution to flow into the waste liquid reservoir chamber 29. At this time, since the cross sectional area of the discharge flow channel 26 is smaller than that of the waste liquid reservoir chamber 29, the nucleic acid specimen solution does not flow back into the reaction chamber 24 due to the resistance of the discharge flow channel 26 and hence is held to the bottom of the waste liquid reservoir chamber 29.

As described above, it is possible to provide a biochemical reaction cassette 21 with an improved liquid filling performance by equipping it with a buffer section 27 that is inclined toward the discharge flow channel 26 at the ceiling. Additionally, it is possible to improve the performance of the biochemical reaction cassette 21 for supplying and discharging liquid by connecting a liquid reservoir chamber 28 to the reaction chamber 24 by way of the injection flow channel 25 and a waste liquid reservoir chamber 29 to the buffer section 27 by way of the discharge flow channel 26. Still additionally, since the biochemical reaction cassette 21 has a structure that allows it to be manufactured by means of a metal mold, it is possible to reduce the manufacturing cost of the biochemical reaction cassette 21.

Fourth Embodiment

Figure 9A:
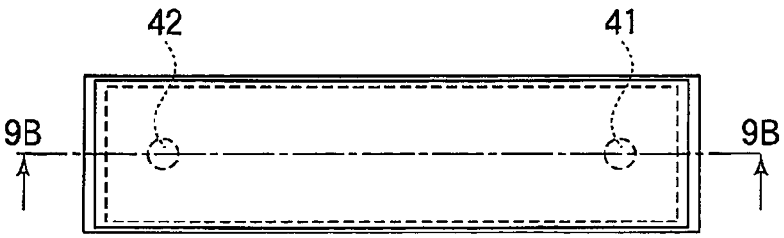
FIGS. 9A, 9B, 9C and 9D are schematic views of the fourth embodiment of biochemical reaction cassette, illustrating the structure thereof.
Figure 9C:
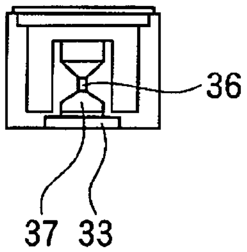
Figure 9B:
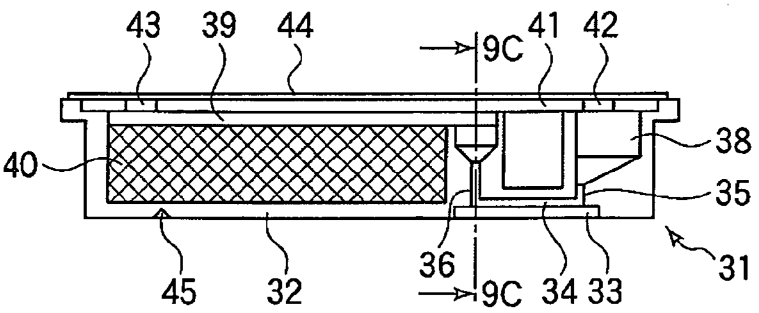
Figure 9D:
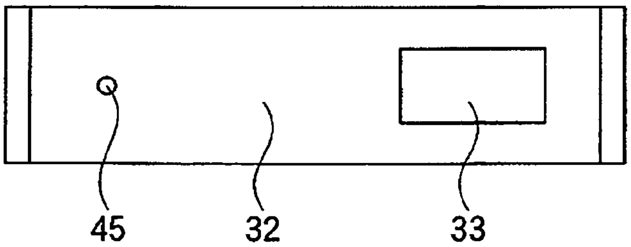

FIGS. 9A, 9B, 9C and 9D are schematic views of the fourth embodiment of biochemical reaction cassette, illustrating the structure thereof. FIG. 9A is a plan view. FIG. 9B is a cross sectional view taken along line 9B-9B in FIG. 9A. FIG. 9C is a cross sectional view taken along line 9C-9C in FIG. 9B. FIG. 9D is a bottom view. The biochemical reaction cassette 31 comprises a housing 32 and a glass substrate 33, which is bonded to the housing 32 and to which a DNA probe that is to specifically bind to a target nucleic acid is immobilized. Since this embodiment is provided with a reaction chamber 34, an injection flow channel 35, a discharge flow channel 36 and a buffer section 37, which are like those of the second embodiment, they will not be described here any further. A liquid reservoir chamber 38 is connected to the end (upper end) of the injection flow channel 35 opposite to the end thereof connected to the reaction chamber 34. A waste liquid reservoir chamber 39 is connected to the end (upper end) of the discharge flow channel 36 opposite to the end thereof connected to the buffer section 37. An absorbent 40 made of PP (polypropylene) fiber is contained in the inside of the waste liquid reservoir chamber 39 to absorb waste liquid. As shown in FIG. 9B, a resin-made closure member 41 is welded to the housing 32 by means of ultrasonic welding so that the air-tightness of the welded part of the housing 32 and the closure member 41 is guaranteed. The closure member 41 is provided with a hole 42 at a position connected to the liquid reservoir chamber 38. The closure member 41 is provided with a hole 43 at a position connected to the waste liquid reservoir chamber 39. In FIG. 9B, reference character 44 denotes a sealing member made of aluminum foil that is bonded to the entire surface area of the closure member 41 to cover the hole 42 and the another hole 43 of the closure member 41. As shown in FIG. 9D, the housing 32 is provided at the bottom surface thereof with a dent section 45. The dent section 45 preferably has a sloped surface and shows a conical or frusto-conical cross section as seen from FIG. 9B.

Figure 10:
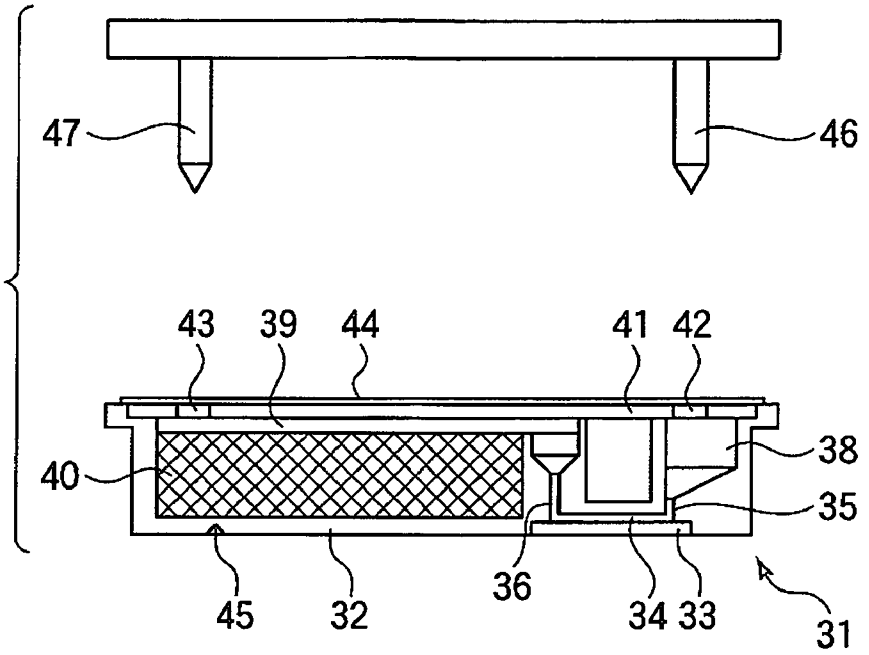
FIG. 10 is a schematic illustration of a principal part of the fourth embodiment, showing how the biochemical reaction cassette is processed.

This biochemical reaction cassette 31 is designed not to function by itself but to do so when used with a biochemical reaction apparatus. FIG. 10 is a schematic illustration of a principal part of the biochemical reaction cassette 31 of the fourth embodiment, showing how it is processed in a biochemical reaction apparatus. The components of the biochemical reaction cassette 31 are described above by referring to FIGS. 9A through 9D and hence will not be described here any further. The biochemical reaction cassette 31 is arranged in the inside of a biochemical reaction apparatus (not shown), which is provided with hole making means 46 and 47 for cutting the sealing member 44 that covers the holes 42 and 43 of the closure member 41 of the biochemical reaction cassette 31 to produce holes through it. As the holes are formed through the sealing member 44, the liquid reservoir chamber 38 and the waste liquid reservoir chamber 39 in the biochemical reaction cassette 31 communicate with the atmosphere by way of the holes formed through the sealing member 44 that used to cover the holes 42 and 43 of the closure member 41.

Figure 11:
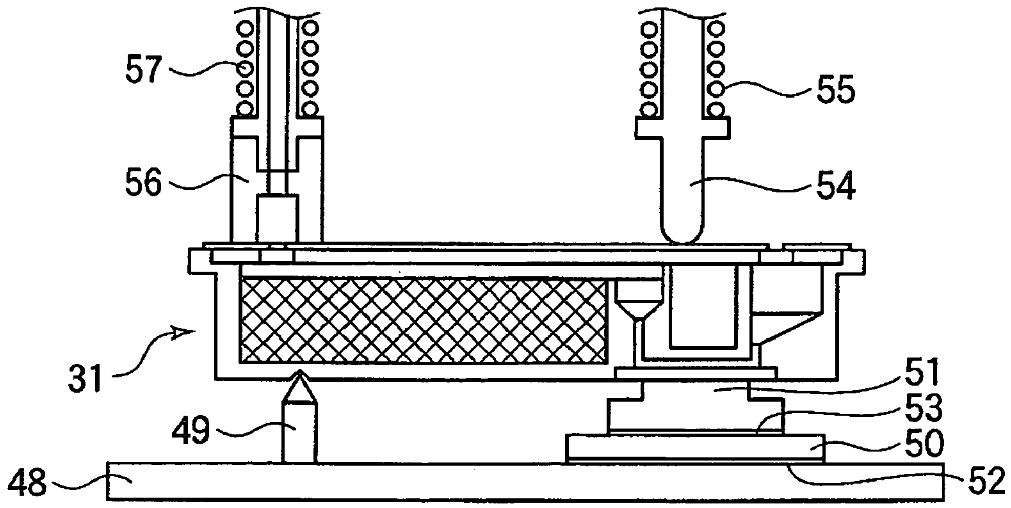
FIG. 11 is a schematic illustration of a principal part of the fourth embodiment, also showing how the biochemical reaction cassette is processed.

FIG. 11 is a schematic illustration of a principal part of the biochemical reaction cassette 31 of the fourth embodiment, also showing how the biochemical reaction cassette 31 is processed in a biochemical reaction apparatus. More specifically, it shows the process for causing the target nucleic acid to form a hybrid with the probe immobilized to the surface of the glass substrate by way of a hybridization reaction. The components of the biochemical reaction cassette 31 are described above by referring to FIGS. 9A through 9D and hence will not be described here any further by using reference characters. In FIG. 11, reference character 48 denotes the base of a station for causing a hybridization reaction to take place (to be referred to as hybridization station hereinafter). Reference character 49 denotes a support means having a front part that has a sloped surface and shows a conical or frusto-conical profile so as to be engaged with a dent section 45 formed at the bottom surface of the biochemical reaction cassette 31. Reference character 50 denotes a Peltier element and reference character 51 denotes an aluminum-made thermal block. Highly thermally conductive elastic sheets 52 and 53 are sandwiched respectively between the base 48 and the Peltier element 50 and between the Peltier element 50 and the thermal block 51. The biochemical reaction cassette 31 is set in position on the hybridization station as it is engaged at the dent section 45 thereof with the front end of the support means 49 and the glass substrate of the biochemical reaction cassette 31 immobilizing the probe is held at the rear surface (exposed surface) thereof in surface-contact with the thermal block 51. Reference character 54 denotes a pressurizing rod and reference character 55 denotes a pressurizing spring. These components are arranged at the side of the biochemical reaction apparatus and form a pressurizing means that is driven to move up and down by a drive means (not shown). The pressurizing rod 54 is made to abut the closure member 41 of the biochemical reaction cassette 31 and apply downwardly directed force to the entire biochemical reaction cassette 31 so as to hold the glass substrate that immobilizes the probe in tight contact with the thermal block 51. Reference character 56 denotes a cylindrical connection cap made of rubber and reference character 57 denotes a pressurizing spring. These components are arranged at the side of the biochemical reaction apparatus and form a connection means that is driven to move up and down by a drive means (not shown). The connection cap 56 is made to abut the hole 43 of the closure member 41 of the biochemical reaction cassette 31 to connect the waste liquid reservoir chamber 39 and the pressurizing/depressurizing means (not shown) arranged at the side of the biochemical reaction apparatus to each other. The connection cap 56 applies downwardly directed force to the biochemical reaction cassette 31 so as to keep the dent section 45 tightly engaged with front end of the support means 49. As described above, the dent section 45 has a sloped surface and shows a conical or frusto-conical profile. On the other hand, the support means has a front part that has a sloped surface and shows a conical or frusto-conical profile. Therefore, when the biochemical reaction cassette 31 is set in position on the hybridization station, the dent section 45 and the support means 49 trace and become engaged with each other so that they can be aligned with each other accurately if their relative positions are inaccurate to some extent in the initial stages of the engaging operation. Additionally, the biochemical reaction cassette 31 would not come off from the right position if the biochemical reaction apparatus is unexpectedly subjected to an impact or vibrations after the biochemical reaction cassette 31 is set in position on the hybridization station.

Now, the operation of the apparatus will be described by referring to FIGS. 9A through 9D showing the structure of the biochemical reaction cassette.

To fill the reaction chamber 34 of the biochemical reaction cassette 31 with a nucleic acid specimen solution, firstly the nucleic acid specimen solution is supplied to the liquid reservoir chamber 38 by way of the hole 42 of the closure member 41 by a liquid supply means (not shown) such as a pipette tip. At this time, since the cross sectional area of the injection flow channel 35 is smaller than that of the liquid reservoir chamber 38, the nucleic acid specimen solution does not flow into the reaction chamber 24 if the nucleic acid specimen solution is simply supplied into the liquid reservoir chamber due to the resistance of the injection flow channel 35. However, the nucleic acid specimen solution is introduced into the reaction chamber 34 and the buffer section 37 as negative pressure is applied to the side of the waste liquid reservoir chamber 39 by the pressurizing/depressurizing means (not shown) arranged at the side of the biochemical reaction apparatus. Again, on the principle same as the one described above for the second embodiment, no gas is left in the reaction chamber 34 and the reaction chamber 34 can be completely filled with the nucleic acid specimen solution. A hybridization reaction is made to take place under the condition where both the reaction chamber 34 and the buffer section 37 are filled with the nucleic acid specimen solution while the thermal block 51 heats or cools the glass substrate 33 to the desired temperature level. When the hybridization reaction comes to an end, the side of the waste liquid reservoir chamber 39 is brought under negative pressure once again by the pressurizing/depressurizing means (not shown) to cause the nucleic acid specimen solution to flow into the waste liquid reservoir chamber 39. At this time, since the cross sectional area of the discharge flow channel 36 is smaller than that of the waste liquid reservoir chamber 39, the nucleic acid specimen solution does not flow back into the reaction chamber 34 due to the resistance of the discharge flow channel 36 and hence is held to the bottom of the waste liquid reservoir chamber 39.

As described above, it is possible to provide a biochemical reaction cassette 31 with an improved liquid filling performance by equipping it with a buffer section 37 that is inclined toward the discharge flow channel 36 at the ceiling. Additionally, it is possible to improve the performance of the biochemical reaction cassette 31 for supplying and discharging liquid by connecting a liquid reservoir chamber 38 to the reaction chamber 34 by way of the injection flow channel 35 and a waste liquid reservoir chamber 39 to the buffer section 37 by way of the discharge flow channel 36. Still additionally, since the biochemical reaction cassette 31 has a structure that allows it to be manufactured by means of a metal mold, it is possible to reduce the manufacturing cost of the biochemical reaction cassette 31.

The present invention is not limited to the above embodiments and various changes and modifications can be made within the spirit and scope of the present invention. Therefore, to apprise the public of the scope of the present invention, the following claims are made.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2005-266023, filed Sep. 13, 2005, which is hereby incorporated by reference herein in its entirety.

What is claimed is:

1. A biochemical reaction cassette comprising:

a housing member;

a reaction chamber arranged in the housing member and having a bottom section and a ceiling facing the bottom section;

an injection port arranged at the ceiling of the reaction chamber;

a discharge port arranged at the ceiling of the reaction chamber; and a probe carrier arranged at the bottom section of the reaction chamber, wherein the ceiling has an inclination with the highest part located at the discharge port in the vertical direction.

2. The biochemical reaction cassette according to claim 1, wherein the reaction chamber includes a dent section formed on the housing member and a closure section for covering the aperture of the dent section and hermetically sealing the inside from the outside and the closure section includes the probe carrier.

3. The biochemical reaction cassette according to claim 1, wherein the ceiling of the reaction chamber is inclined from the injection port toward the discharge port.

4. The biochemical reaction cassette according to claim 1, wherein the reaction chamber has at part of the ceiling an inclined section inclined toward the discharge port.

5. The biochemical reaction cassette according to claim 1, further comprising:

a liquid reservoir chamber for injection arranged above the reaction chamber in the vertical direction;

the reaction chamber and the liquid reservoir chamber for injection being connected to each other by way of an injection flow channel having an end at the injection port.

6. The biochemical reaction cassette according to claim 5, further comprising:

a waste liquid reservoir chamber arranged above the reaction chamber;

the reaction chamber and the waste liquid reservoir chamber being connected to each other by way of a discharge flow channel having an end at the discharge port.

7. The biochemical reaction cassette according to claim 1, wherein the reaction chamber has a tapered profile and the cross sectional area of the reaction chamber as taken along a plane perpendicular to the moving direction of liquid from the injection port to the discharge port is gradually reduced.

* * * * *